(12) United States Patent
Sleva et al.

(10) Patent No.: US 8,313,687 B2
(45) Date of Patent: Nov. 20, 2012

(54) METHOD OF MAKING AN IMPROVED BALLOON CUFF TRACHEOSTOMY TUBE

(75) Inventors: Michael Sleva, Atlanta, GA (US); James F. Schumacher, Cumming, GA (US); Scott M. Teixeira, Cumming, GA (US); Michael A. Kenowski, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 359 days.

(21) Appl. No.: 12/206,583

(22) Filed: Sep. 8, 2008

(65) Prior Publication Data

US 2009/0091066 A1 Apr. 9, 2009

Related U.S. Application Data

(60) Provisional application No. 60/994,664, filed on Sep. 20, 2007.

(51) Int. Cl.
*B29D 22/02* (2006.01)

(52) U.S. Cl. ........... 264/535; 264/541; 128/207.14; 128/207.15; 604/103.06; 604/103.07

(58) Field of Classification Search ............... 264/535; 128/207.15; 604/103.06, 103.07
See application file for complete search history.

(56) References Cited

U.S. PATENT DOCUMENTS

| | | |
|---|---|---|
| 2,693,182 A | 11/1954 | Phillips |
| 3,481,339 A | 12/1969 | Millet Puig |
| 3,543,751 A | 12/1970 | Sheffer |
| 3,659,612 A | 5/1972 | Shiley et al. |
| 3,688,774 A | 9/1972 | Akiyama |
| 3,693,624 A | 9/1972 | Shiley et al. |
| 3,731,692 A | 5/1973 | Goodyear |
| 3,889,688 A | 6/1975 | Eamkaow |
| 3,901,246 A | 8/1975 | Wallace |
| 3,973,569 A | 8/1976 | Sheridan et al. |
| 3,987,798 A | 10/1976 | McGinnis |
| 4,009,720 A | 3/1977 | Crandall |

(Continued)

FOREIGN PATENT DOCUMENTS

CA 2 296 308 A1 2/1999

(Continued)

OTHER PUBLICATIONS

American Society for Testing Materials (ASTM) Designation: D 790-99, "Standard Test Methods for Flexural Properties of Unreinforced and Reinforced Plastics and Electrical Insulating Materials," pp. 150-158, published Feb. 2000.

(Continued)

*Primary Examiner* — Richard Crispino
*Assistant Examiner* — Elizabeth Royston
(74) *Attorney, Agent, or Firm* — James B. Robinson

(57) ABSTRACT

There is provided a method of making a balloon having a differential thickness. The method uses a raw tube composed of a thermoplastic polymer which is placed in an asymmetrical mold. The tube is preheated in the mold to a temperature sufficient to soften the material of the tube and inflated with a gas to generally uniformly stretch the material of the tube while allowing the tube to retract lengthwise, thus forming a balloon. The resulting completed balloon has a differential wall thickness wherein the upper region has a thickness of from about 15 to about 30 micrometers and the lower region has a thickness of from about 5 to about 15 micrometers.

3 Claims, 8 Drawing Sheets

U.S. PATENT DOCUMENTS

| | | |
|---|---|---|
| 4,018,231 A | 4/1977 | Wallace |
| 4,033,353 A | 7/1977 | La Rosa |
| 4,083,369 A * | 4/1978 | Sinnreich ................ 604/103.06 |
| 4,141,364 A | 2/1979 | Schultze |
| 4,156,428 A | 5/1979 | Henkin |
| 4,178,937 A | 12/1979 | Taylor et al. |
| 4,246,897 A | 1/1981 | Muto |
| 4,248,222 A | 2/1981 | Jaeger et al. |
| 4,270,778 A | 6/1981 | Brownell |
| 4,278,081 A | 7/1981 | Jones |
| 4,280,492 A | 7/1981 | Latham |
| 4,304,228 A | 12/1981 | Depel |
| 4,305,392 A | 12/1981 | Chester |
| 4,327,721 A | 5/1982 | Goldin et al. |
| 4,331,142 A | 5/1982 | Degen |
| 4,340,046 A | 7/1982 | Cox |
| 4,459,984 A | 7/1984 | Liegner |
| 4,471,776 A | 9/1984 | Cox |
| 4,596,248 A | 6/1986 | Lieberman |
| 4,627,433 A | 12/1986 | Lieberman |
| 4,649,913 A | 3/1987 | Watson |
| 4,886,059 A | 12/1989 | Weber |
| 4,979,505 A | 12/1990 | Cox |
| 4,987,895 A | 1/1991 | Heimlich |
| 5,056,515 A | 10/1991 | Abel |
| 5,067,496 A | 11/1991 | Eisele |
| 5,067,497 A | 11/1991 | Greear et al. |
| 5,285,777 A | 2/1994 | Beckwith |
| 5,311,864 A | 5/1994 | Huerta |
| 5,334,146 A * | 8/1994 | Ozasa ................ 604/103.06 |
| 5,339,809 A | 8/1994 | Beck, Jr. et al. |
| 5,443,064 A | 8/1995 | Theis et al. |
| 5,458,139 A | 10/1995 | Pearl |
| 5,501,215 A | 3/1996 | Huerta |
| 5,653,230 A | 8/1997 | Ciaglia et al. |
| 5,653,231 A | 8/1997 | Bell |
| D398,989 S | 9/1998 | Ashlin |
| 5,819,734 A | 10/1998 | Deily et al. |
| 6,053,167 A | 4/2000 | Waldeck |
| 6,105,577 A | 8/2000 | Varner |
| 6,135,111 A | 10/2000 | Mongeon |
| 6,248,099 B1 | 6/2001 | Bell |
| 6,284,179 B1 | 9/2001 | Deily et al. |
| 6,286,509 B1 | 9/2001 | Nash et al. |
| 6,460,540 B1 | 10/2002 | Klepper |
| 6,526,977 B1 * | 3/2003 | Gobel ................ 128/207.14 |
| 6,612,305 B2 * | 9/2003 | Fauza ................ 128/200.26 |
| 6,637,435 B2 | 10/2003 | Hague et al. |
| 6,662,804 B2 | 12/2003 | Ortiz |
| 6,725,862 B2 | 4/2004 | Klinberg et al. |
| 6,745,773 B1 | 6/2004 | Gobel |
| 6,814,077 B1 | 11/2004 | Eistert |
| 6,840,242 B1 | 1/2005 | McCoy |
| 6,971,382 B1 | 12/2005 | Corso |
| 7,036,510 B2 | 5/2006 | Zgoda et al. |
| 7,037,562 B2 | 5/2006 | Jimenez |
| 7,040,321 B2 | 5/2006 | Göbel |
| 7,086,402 B2 | 8/2006 | Peterson |
| 7,195,016 B2 | 3/2007 | Loyd et al. |
| 2001/0022415 A1 | 9/2001 | Laksin |
| 2002/0014238 A1 | 2/2002 | Kotmel |
| 2003/0066532 A1 | 4/2003 | Gobel |
| 2003/0139762 A1 | 7/2003 | Lee |
| 2005/0065468 A1 | 3/2005 | Goebel |
| 2005/0166926 A1 | 8/2005 | Nomori |
| 2006/0157061 A1 | 7/2006 | Loyd et al. |
| 2006/0184109 A1 | 8/2006 | Gobel |
| 2007/0027520 A1 * | 2/2007 | Sherburne ................ 623/1.11 |
| 2007/0095351 A1 | 5/2007 | Gobel |
| 2007/0289596 A1 | 12/2007 | Campbell et al. |
| 2007/0296125 A1 * | 12/2007 | Colburn et al. ................ 264/562 |
| 2008/0092902 A1 | 4/2008 | Schnell |
| 2008/0142016 A1 | 6/2008 | Colburn et al. |
| 2009/0025729 A1 | 1/2009 | Nomori |
| 2009/0090365 A1 | 4/2009 | Cuevas et al. |
| 2009/0090366 A1 | 4/2009 | Cuevas et al. |
| 2009/0209908 A1 | 8/2009 | Cuevas et al. |

FOREIGN PATENT DOCUMENTS

| | | |
|---|---|---|
| CA | 2 353 007 A1 | 6/2000 |
| DE | 44 01 904 A1 | 7/1995 |
| EP | 0 037 719 A1 | 10/1981 |
| EP | 0 052 483 A1 | 5/1982 |
| EP | 0 072 230 A1 | 2/1983 |
| EP | 0 078 685 A1 | 5/1983 |
| EP | 0 106 780 A1 | 4/1984 |
| EP | 0 107 779 A1 | 5/1984 |
| EP | 0 155 331 A1 | 9/1985 |
| EP | 0 371 752 A1 | 6/1990 |
| EP | 0 489 507 A1 | 6/1992 |
| EP | 0 586 717 A1 | 3/1994 |
| EP | 0 598 948 A1 | 6/1994 |
| EP | 0 747 077 A2 | 12/1996 |
| EP | 0 768 096 A2 | 4/1997 |
| EP | 1 004 328 A1 | 5/2000 |
| EP | 1 005 877 A2 | 6/2000 |
| EP | 1 044 701 A2 | 10/2000 |
| EP | 1 210 953 A1 | 6/2002 |
| EP | 1 219 317 A2 | 7/2002 |
| EP | 1 329 239 A1 | 7/2003 |
| EP | 1 803 478 A1 | 7/2007 |
| EP | 1 806 158 A1 | 7/2007 |
| GB | 0 019 196 A | 0/1907 |
| GB | 1 040 425 A | 8/1966 |
| GB | 1 113 484 A | 5/1968 |
| GB | 1 153 863 A | 5/1969 |
| GB | 2 056 285 A | 3/1981 |
| GB | 2 174 303 A | 11/1986 |
| GB | 2 324 735 A | 11/1998 |
| GB | 2 335 362 A | 9/1999 |
| GB | 2 429 919 A | 3/2007 |
| JP | 05-031192 A | 2/1993 |
| JP | 10-005340 A | 1/1998 |
| JP | 10-337326 A | 12/1998 |
| JP | 2003-093512 A | 4/2003 |
| JP | 2005-270319 A | 10/2005 |
| WO | WO 80/00307 A1 | 3/1980 |
| WO | WO 84/02657 A1 | 7/1984 |
| WO | WO 87/01293 A1 | 3/1987 |
| WO | WO 89/12425 A1 | 12/1989 |
| WO | WO 91/06342 A1 | 5/1991 |
| WO | WO 92/07602 A1 | 5/1992 |
| WO | WO 93/24170 A1 | 12/1993 |
| WO | WO 94/15657 A1 | 7/1994 |
| WO | WO 96/37250 A1 | 11/1996 |
| WO | WO 96/40339 A1 | 12/1996 |
| WO | WO 96/40340 A2 | 12/1996 |
| WO | WO 99/32169 A1 | 7/1999 |
| WO | WO 99/38548 A2 | 8/1999 |
| WO | WO 99/53989 A1 | 10/1999 |
| WO | WO 00/32262 A1 | 6/2000 |
| WO | WO 00/62849 A1 | 10/2000 |
| WO | WO 01/24861 A1 | 4/2001 |
| WO | WO 01/83015 A1 | 11/2001 |
| WO | WO 02/28462 A1 | 4/2002 |
| WO | WO 2004/016308 A2 | 2/2004 |
| WO | WO 2004/060439 A2 | 7/2004 |
| WO | WO 2004/069316 A2 | 8/2004 |
| WO | WO 2004/071553 A2 | 8/2004 |
| WO | WO 2004/096330 A2 | 11/2004 |
| WO | WO 2004/096331 A2 | 11/2004 |
| WO | WO 2004/101046 A1 | 11/2004 |
| WO | WO 2004/101048 A2 | 11/2004 |
| WO | WO 2005/016427 A2 | 2/2005 |
| WO | WO 2005/058401 A1 | 6/2005 |
| WO | WO 2006/029070 A2 | 3/2006 |
| WO | WO 2006/037626 A2 | 4/2006 |
| WO | WO 2006/087032 A1 | 8/2006 |
| WO | WO 2006/089961 A1 | 8/2006 |
| WO | WO 2006/099434 A1 | 9/2006 |
| WO | WO 2006/100426 A1 | 9/2006 |
| WO | WO 2006/125006 A2 | 11/2006 |
| WO | WO 2006/138138 A1 | 12/2006 |
| WO | WO 2007/000127 A1 | 1/2007 |
| WO | WO 2007/012060 A2 | 1/2007 |
| WO | WO 2007/016335 A1 | 2/2007 |
| WO | WO 2007/017447 A2 | 2/2007 |

| | | |
|---|---|---|
| WO | WO 2007/024315 A1 | 3/2007 |
| WO | WO 2007/062162 A1 | 5/2007 |
| WO | WO 2007/069766 A1 | 6/2007 |
| WO | WO 2007/092199 A2 | 8/2007 |
| WO | WO 2007/149202 A1 | 12/2007 |
| WO | WO 2007/149203 A2 | 12/2007 |
| WO | WO 2007/149301 A2 | 12/2007 |
| WO | WO 2008/034751 A1 | 3/2008 |
| WO | WO 2008/034872 A1 | 3/2008 |
| WO | WO 2008/042130 A1 | 4/2008 |
| WO | WO 2008/042133 A2 | 4/2008 |
| WO | WO 2008/047978 A1 | 4/2008 |

OTHER PUBLICATIONS

American Society for Testing Materials (ASTM) Designation: D1238-04c, "Standard Test Method for Melt Flow Rates of Thermoplastics by Extrusion Plastometer," pp. 1-14, published Dec. 2004.

American Society for Testing Materials (ASTM) Designation: D2240-05, "Standard Test Method for Rubber Property—Durometer Hardness," pp. 1-13, published Sep. 2005.

* cited by examiner

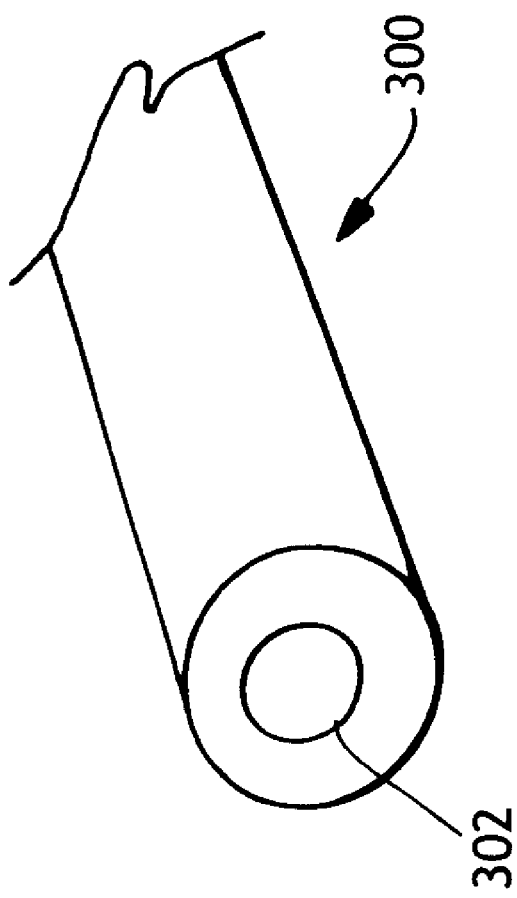
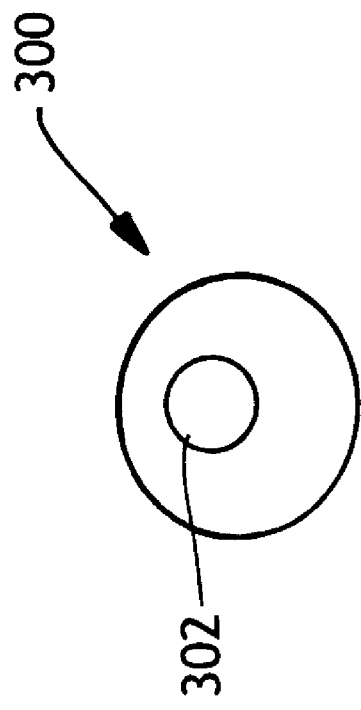

METHOD OF MAKING AN IMPROVED BALLOON CUFF TRACHEOSTOMY TUBE

This application claims the benefit of commonly assigned U.S. provisional application 60/994,664, filed Sep. 20, 2007.

BACKGROUND OF THE INVENTION

Cuffed tracheostomy (trach) tubes are often used to ventilate hospitalized patients for longer periods of time; endotracheal (ET) tubes being used for periods less than a week to 10 days. Trach tubes are inserted through the throat, into the trachea and the proximal end then typically connected to a mechanically supplied source of breathing air, i.e., from a ventilator or respirator. The cuffs or "balloons" are located on the distal end of the trach tube and block the patient's trachea so that inhalation and exhalation are performed only through the tube. The balloon also functions to block liquid secretions from passing downwardly into the lungs and potentially causing ventilator acquired pneumonia (VAP). Secretions are held above the balloon and may be periodically removed to help ensure they do not enter the lungs.

Cuffs for use on ET and trach tubes were, for many years, high-pressure, low-volume balloons. These balloons also had relatively thick walls made from polyolefins and polyvinyl chlorides. Wall thicknesses could be of the order of from 60 to 150 microns or more, making for a relatively cumbersome balloon but one that was unmistakably strong. These "HPLV" balloons were found to be the cause of substantial trauma to the tracheal tissue since they forcefully compressed the tracheal walls. Adverse patient outcomes and lengthened recovery times prompted medical professionals and researchers to search for a less traumatic device with which to obdurate the trachea for assisted mechanical ventilation.

In the last few decades balloons have been developed that are much lower in pressure and higher in volume. These HVLP balloons present a greater surface area of contact with the tracheal wall and so are able to lay against the wall using much less pressure per square centimeter. These balloons, however, remained relatively thick; still on the order of 60 to 150 microns. Trauma was positively impacted by these newer balloons though room for improvement remained.

A more recent development in has been thinner walled HVLP balloons like those disclosed in U.S. Pat. No. 6,526,977 to Gobel. Gobel teaches oversized balloons with a wall thickness so low that they form folds against the tracheal wall that are so small that secretions cannot pass through. Likewise, U.S. Pat. No. 6,612,305 teaches a recently developed balloon that provides better control over the location of the balloon but that appears to seal the tracheal stoma, thus limiting access to that region.

A balloon and a method of making a balloon that is more stable in the trachea than current balloons, and that is thin and compliant would therefore be desirable.

SUMMARY

The subject of the present disclosure relates to a method of making a balloon cuffed tracheostomy tube with a balloon designed to enhance the controlled location of the tube in the trachea but without sealing the tracheal stoma.

The tracheostomy tube device includes a hollow tube having a proximal end portion, a distal end portion, and a bend region intermediate of the end portions. The distal end portion of the tube is arranged for insertion through a patient's throat and tracheal stoma and into the tracheal lumen such that the distal end portion of the tube extends in a first direction within the tracheal lumen when the proximal end portion extends in a second direction through the tracheal stoma. The proximal end portion defines a proximal plane of the device.

The device further includes an inflatable balloon enveloping a portion of the tube. The balloon has a distal balloon portion substantially centered about and attached to the distal end portion of the tube. The balloon also has a proximal balloon portion attached to the bend region of the tube and positioned substantially off-center about the bend region below the proximal plane of the device. Upon inflation, this configuration provides for expansion of the balloon around the distal end portion of the tube and the proximal end portion of the tube below the proximal plane of the device to seal the trachea below the tracheal stoma and avoid sealing the trachea above the tracheal stoma. This configuration of the balloon on the tube will allow secretions to exit the stoma. The balloon may be inflated and deflated by conventional means.

The present disclosure encompasses a method for making an inflatable balloon component which may further have differential wall thicknesses. The method includes at least the following steps: providing a raw tube composed of a thermoplastic polymer, preheating the raw tube in a mold to a temperature sufficient to soften the material of the tube; inflating the tube with compressed gas to stretch the material of the tube while simultaneously allowing the tube to retract lengthwise, thus forming the balloon. The just-formed balloon may be heat set to orient the amorphous thermoplastic polymer portions in relation to the stretching direction. The balloon may be cooled and removed from the mold.

Accordingly, the inflatable balloon component may include a distal end, a distal attachment zone for attaching the balloon to the tube, a proximal end, a proximal attachment zone for attaching the balloon to the tube, an upper region and a lower region, wherein the upper region has a thickness of from about 15 to about 30 micrometers and the lower region has a thickness of from about 5 to about 15 micrometers.

The balloon may be formed from thermoplastic polyurethane polymers, thermoplastic polyolefin elastomers, thermoplastic polyolefin block copolymers, SBS di-block elastomers, SEBS tri-block elastomers, polyvinyl chloride, polyethylene terephthalate, low density polyethylene and blends and mixtures thereof.

BRIEF DESCRIPTION OF THE DRAWINGS

FIG. 8A and FIG. 8B are each an illustration of cross-section of an asymmetric raw tube.

DETAILED DESCRIPTION

Figure 1:
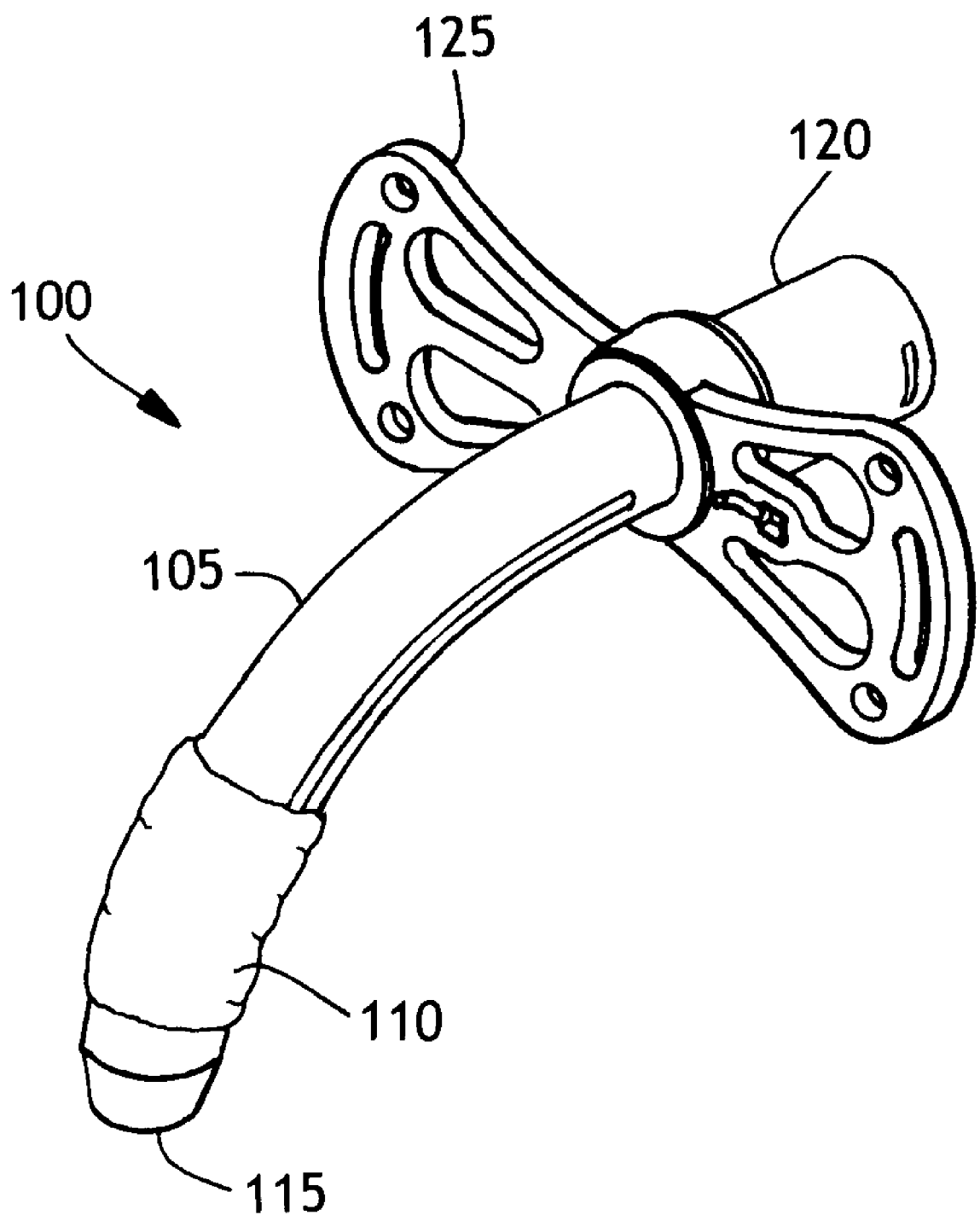
FIG. 1 is an illustration of a cuffed tracheostomy tube.

FIG. 1 is an illustration of a cuffed tracheostomy tube device 100. The device 100 has a tube 105 and an inflatable cuff 110. The tube further has a proximal end 120 and a distal end 115. The tube has a flange 125 near the proximal end that is used to attach the tube to the skin of the patient by suturing. The flange also has slots for use in attaching a strap around the neck of the patient to aid in keeping the trach tube in place. The tube has a lumen through the center that is used for inhalation and exhalation and the proximal end may be attached to a ventilator if needed. Once the tube is placed in the trachea of a patient through the tracheal stoma, the balloon is inflated and the trachea is sealed. Conventional means for inflating the balloon are used and include a small inflation lumen (not shown) along the tube and going through the flange for connection to a source of inflating air.

Figure 2:
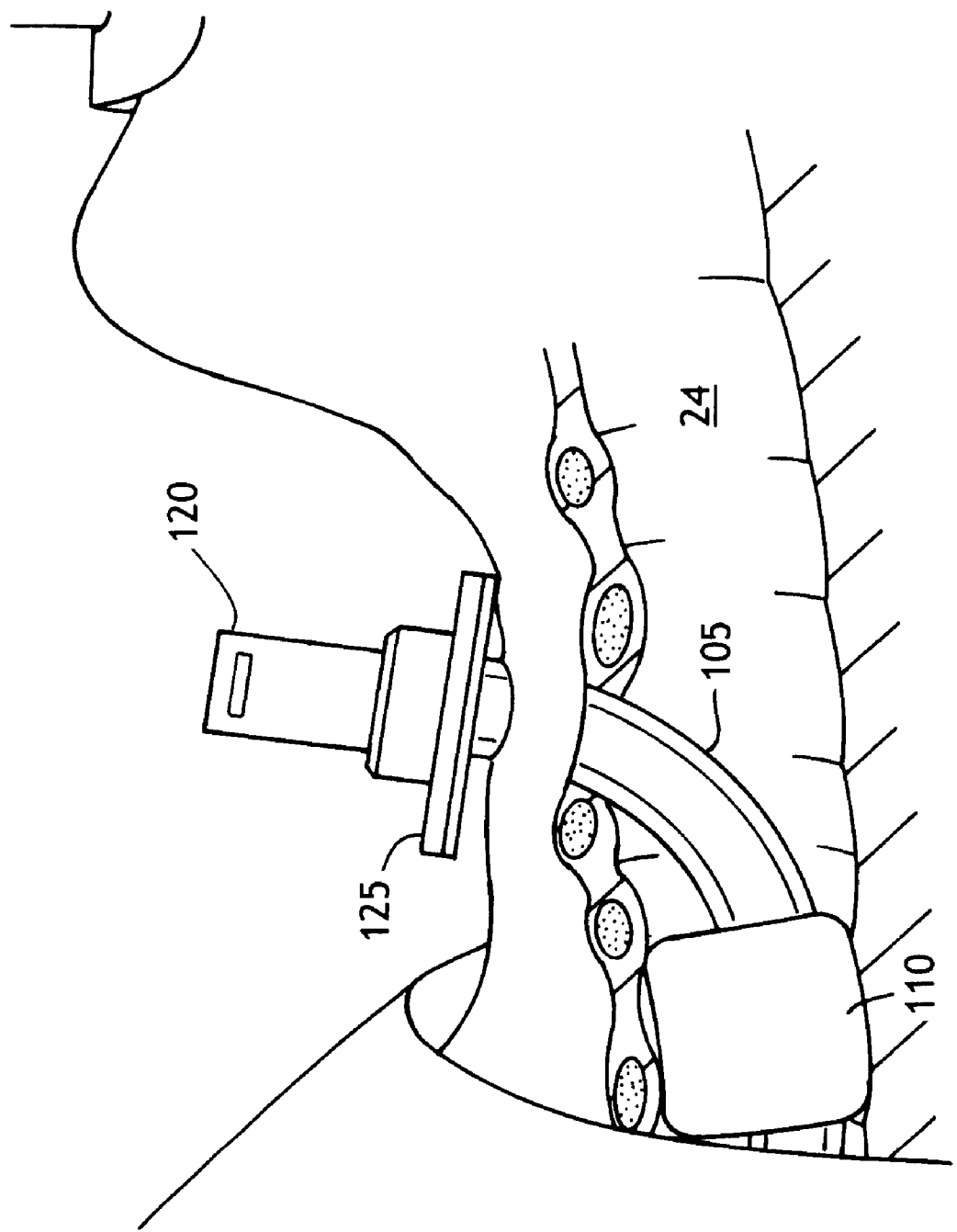
FIG. 2 is an illustration of a cuffed tracheostomy tube after it has been inserted into the trachea and the balloon inflated.

FIG. 2 is an illustration of the device 100 from FIG. 1 after insertion into the trachea 24 and inflation of the balloon 110. The flange 125 rests against the outside of the throat and the balloon 110 seals the trachea 24 so that breathing must be directed through the lumen of the tube 105.

Figure 3:
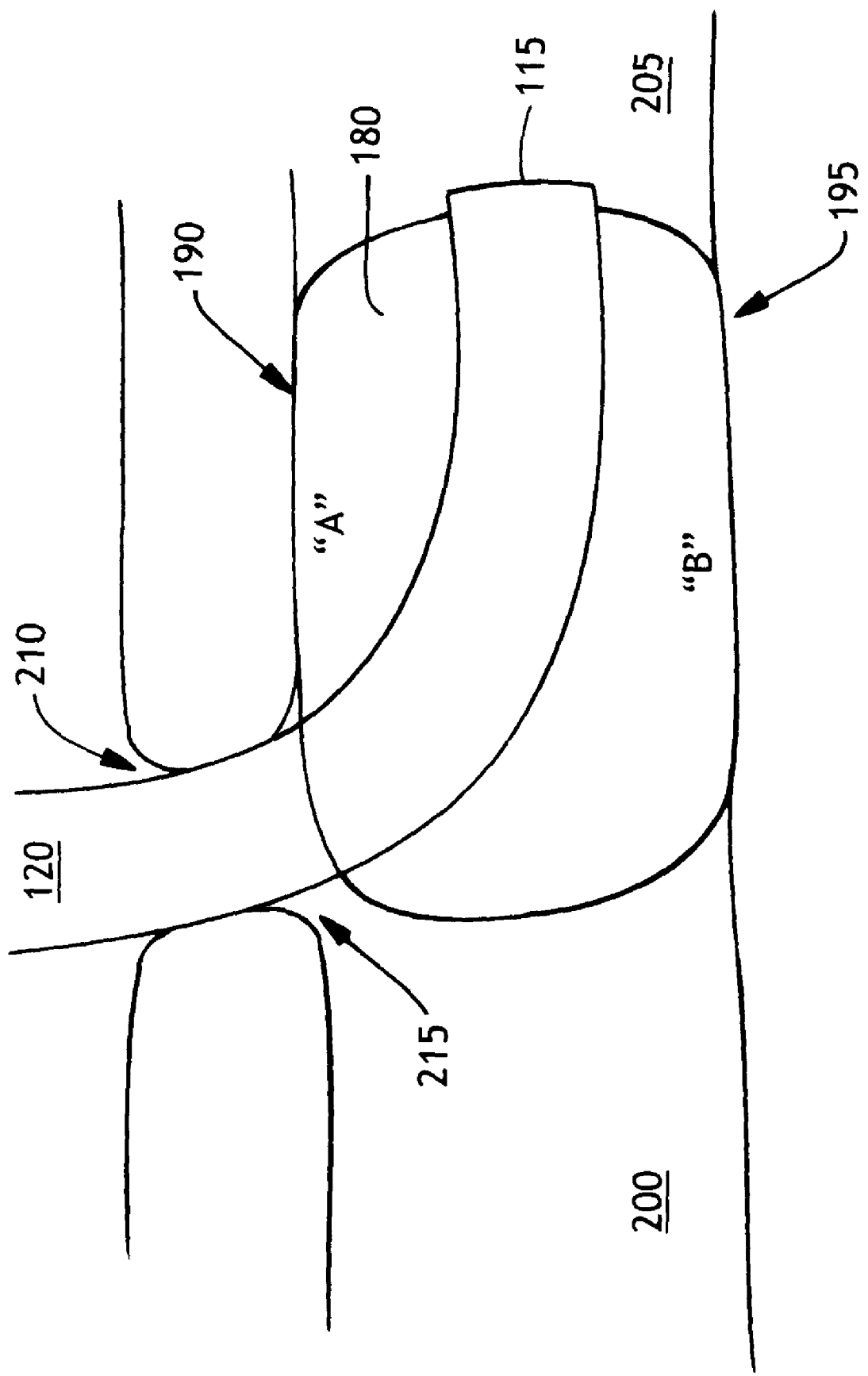
FIG. 3 is an illustration of an exemplary balloon cuffed tracheostomy tube after it has been inserted into the trachea and the balloon inflated. This balloon is designed so as to enhance the tube's anchorability without completely sealing the tracheal stoma.

FIG. 3 is a representation of a balloon on a tube in a trachea according to this disclosure wherein the inflated balloon 180 is adapted to seal the trachea (i.e., the tracheal lumen 200) in the region 205 below the tracheal stoma 210 and to avoid sealing the trachea in the region above the tracheal stoma. This is achieved by the fact that the point of attachment on the proximal end 120 and the point of attachment on the distal end 115 of the inflatable balloon 180 on the tube are not contiguous or, in other words, are at an angle ($\alpha$) other than 180 degrees. This configuration of the balloon should allow secretions to exit the stoma at the opening 215.

It is further desirable that the various areas of the balloon have different thicknesses. The wall of the balloon in continuous area "B" for example, is desirably thinner than the wall of the balloon in continuous area "A". Although the inventors should not be held to a particular theory of operation, it is generally thought that having the relatively thinner second continuous portion "B" of the balloon contacting the lower wall 195 of the trachea will provide a better seal in that region where secretions may be more prone to collect due to gravity when a patient is resting horizontally on his back. The relatively thicker first continuous portion "A" of the balloon contacting the upper wall 190 of the trachea is where secretions may be less prone to collect due to gravity when a patient is resting horizontally on his back. Once the patient moves to an upright position, the secretions should be able to reach the tracheal stoma and exit the trachea at the opening 215.

The disclosure discussed in the Summary encompasses a method for making an inflatable balloon component which may have differential wall thickness. The method includes the step of providing a raw tube composed of a thermoplastic polymer and having a lumen. When the tube is preheated in a mold to a temperature sufficient to soften the material of the tube and inflated with a gas introduced to the raw tube lumen to generally uniformly stretch the material of the tube, the tube forms a balloon taking the shape of the mold and includes a distal end, a distal attachment zone, a proximal end, a proximal attachment zone, an upper region and a lower region. Desirably, the upper region has a thickness of from about 15 to about 30 micrometers and the lower region has a thickness of from about 5 to about 15 micrometers.

The measurement of balloon wall thicknesses may be made using a Litematic device. An exemplary device is the series 318 Model VL-50A by Mitutoyo America Corporation. According to the manufacturer, the Litematic device measures thicknesses between 0 and 50.8 mm with a resolution of 0.01 micron, using a probe tip and an inflexible ceramic base. The measuring force used is 0.01N (1 gram). The probe tip used for testing herein was a 3 mm diameter carbide ball contact point which was provided as the "standard" probe tip with the Litematic device.

Strips of single-ply foils or membranes may be used to determine the thickness of each sample. Balloon specimens (not attached to a trach tube) from each sample may be cut to prepare the strips: first the ends should be cut off to leave a uniform band of about 30 mm in width; then each band should be cut in the width direction to form a strip. Thickness measurements at 10 locations along the length of each strip should be made, the individual measurements of strips for each sample (with at least 6 strips measured) should be averaged together, and the respective standard deviations calculated.

Figure 4:
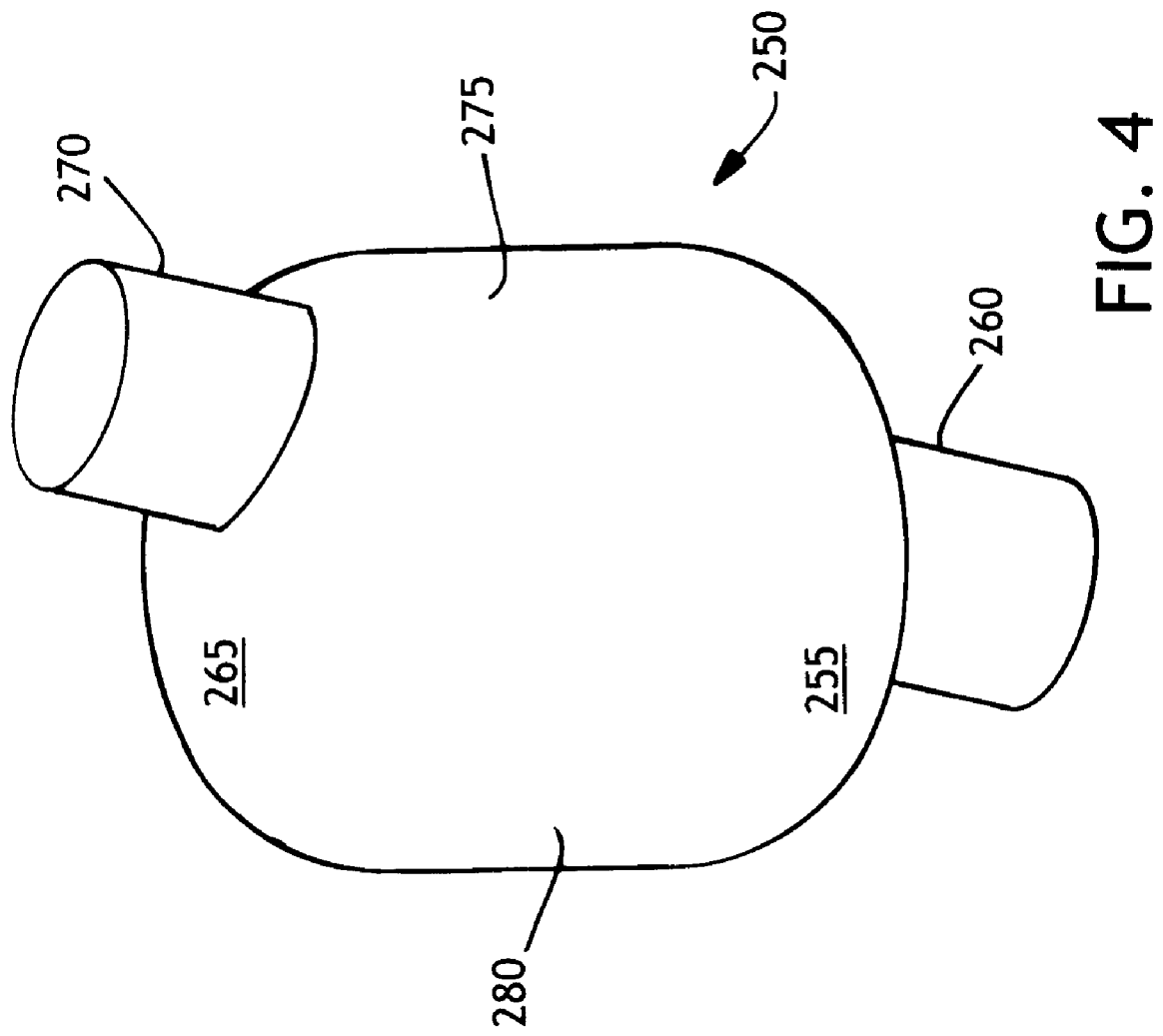
FIG. 4 is a perspective view of an exemplary inflatable balloon component.
Figure 5:
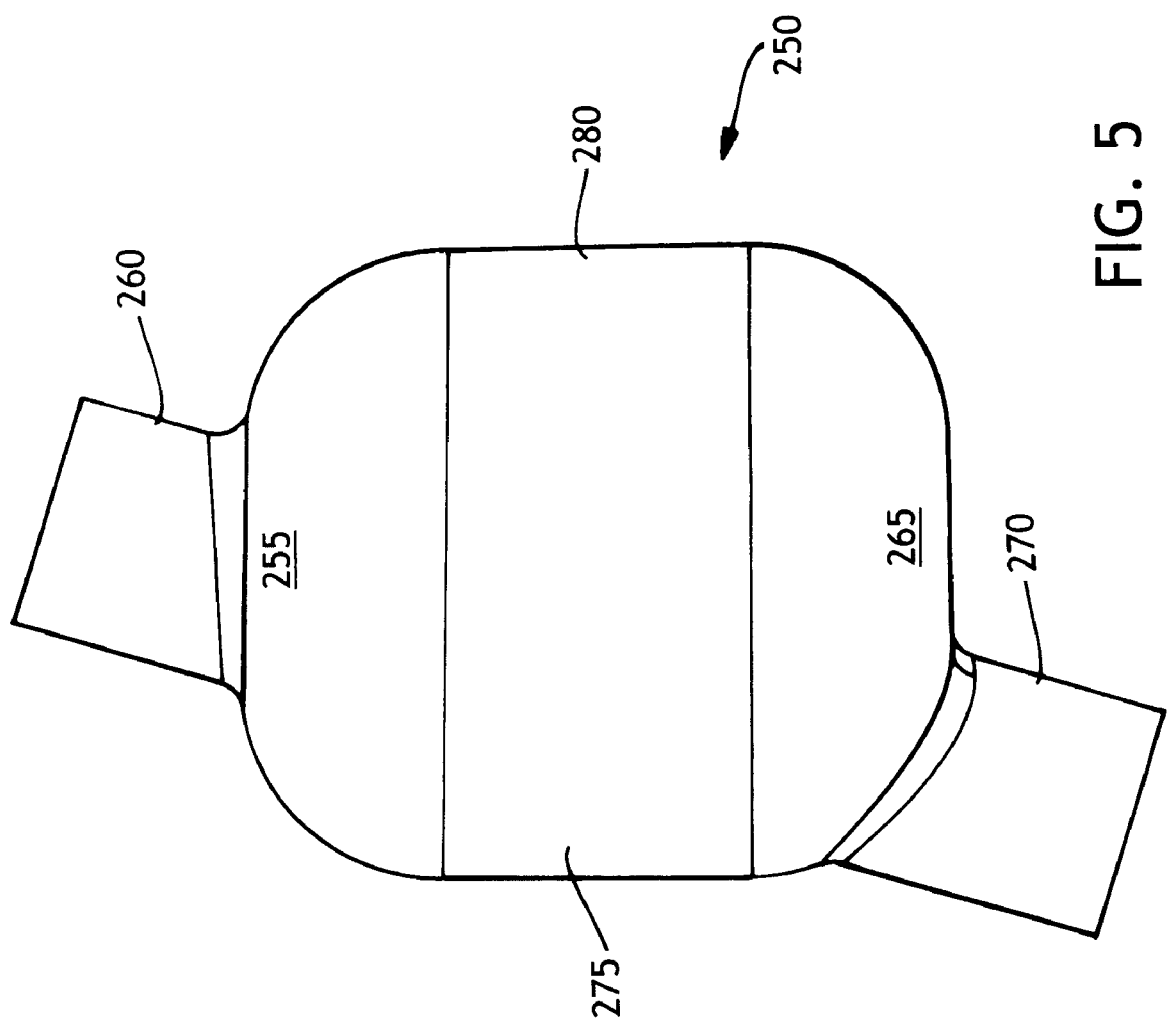
FIG. 5 which is a side view of an exemplary inflatable balloon component.

FIGS. 4 and 5 are views of a balloon formed by the disclosed method. The mold used to form this balloon is, of course, the same shape as the balloon that is desired, i.e., at least one of the ends of the tubing is off-set from the centerline of the mold so that the off-set balloon may be formed. FIGS. 4 and 5 are, therefore, not only drawings of the balloon but representations of the void space of the mold as well. In order to form the balloon with at least one opening on the end that is offset from the centerline of the balloon, the mold must be asymmetric, i.e., the tubing is placed in the mold so that it travels in a straight line through the void space of the mold with the tubing ends off-set from the centerline of the mold as desired. The mold has openings on each end through which the tubing may protrude and be clamped. The mold may be capable of being opened in two or more pieces or may be a single piece. If the mold is capable of being opened, the tubing is placed in the mold and the mold closed. If it is a single piece the tubing may be slid into the mold from an either end.

According to the method, the raw tube is preheated in the mold to a temperature sufficient to soften the material of the tube. The tubing may have walls that are symmetrical in thickness and its size (diameter) will be determined by the size of cuff that is desired. For example, a size 9 trach tube may be made with a raw tube having an 8.61 mm outer diameter (OD) and an inner diameter (ID) of 8.5 mm. After the tube is placed in the mold with enough material protruding from each end to allow it to be held tightly, the mold and tube are preheated to a temperature between 50 and 120° C., desirably between 60 and 80° C. The preheated raw tube is stretched lengthwise (axially) by pulling the ends. The tube should be stretched by about 50 to 200 percent over a period of between 5 and 60 seconds with pressure applied internally (in the raw tube lumen) with air, nitrogen or another inert gas at about 0.5 bar, while the temperature is maintained. The heated, stretched tube is next pressurized with pressure applied internally with air, nitrogen or another inert gas at a pressure between about 0.5 and 2 bar while being allowed to retract by 10 to 50 percent over a time period of between 5 and 15 seconds, to form the balloon. This retraction/pressurization step allows the tubing to stretch until it contacts the walls of the mold but does not keep it so extended as to be excessively thin and so rupture.

Optionally the balloon may then be heat set by heating it, while still in the mold with its ends fixed, to a temperature of 130-165° C. for a time of about 30-90 seconds and at a pressure to keep the balloon inflated; e.g. about 0.5 bar. The balloon may be cooled at about 20-50° C. and thereafter removed from the mold. If the mold is a one piece mold the balloon should be collapsed so that it may be withdrawn without damage. The balloon may be collapsed by subjecting the tubing to a vacuum and evacuating the interior of the balloon. After the balloon is collapsed it may be easily withdrawn from the mold through either end or entry point of the tubing to the mold. The thus-formed balloon may subsequently be attached to a tube by known means.

Of course, other polymer materials may be used to form the balloon component. For example, the balloon component may be formed from thermoplastic polyurethane polymers, thermoplastic polyolefin elastomers, thermoplastic polyolefin block copolymers, SBS di-block elastomers, SEBS tri-block elastomers, polyvinyl chloride (PVC), polyethylene terephthalate (PET) and blends and mixtures thereof. More desirably, polyurethane may be used because it has been found to cause less irritation to tissues than other materials. Useful polyurethanes include those from the Dow Chemical Company (Dow Plastics) available under the tradename Pellethane®. Pellethane® thermoplastic polyurethane elastomer is available in a number of grades and hardnesses and the particular one selected for a specific use will depend on the properties desired in the final product. The hardness of a polymer, for example, is an attribute that may be varied to meet the requirements of various applications.

EXAMPLE

A raw polyurethane tube made from a Dow polyurethane designated Pellethane® 2363-90A which has a durometer hardness of 90A (ASTM D-2240) was used. This polyurethane has a softening temperature of 110° C. (ASTM D-790) and a melt index of 30 g/10 min. at 224° C., 2160 g (ASTM D-1238). The tube having an 8.61 mm outer diameter (OD) and an inner diameter (ID) of 8.5 mm was placed in a one piece mold with a void space like that of FIG. 4 and clamped at the ends outside the mold. The mold and tubing were preheated to a temperature of about 60° C. Once equilibrium was reached the tubing was stretched by about 75 percent under slight internal pressure; 0.5 bar using nitrogen, in a time of about 10 seconds. The tubing was allowed to retract by about a third as it was internally pressurized at 2 bar to form the balloon. The balloon was heat set at a temperature of about 140° C. for a time of about 90 seconds at a pressure of about 0.5 bar. The balloon was cooled at about 45° C., a vacuum was applied to the lumen of the tubing to collapse the balloon and the tubing and balloon removed from the mold through one of the ends.

Figure 6:
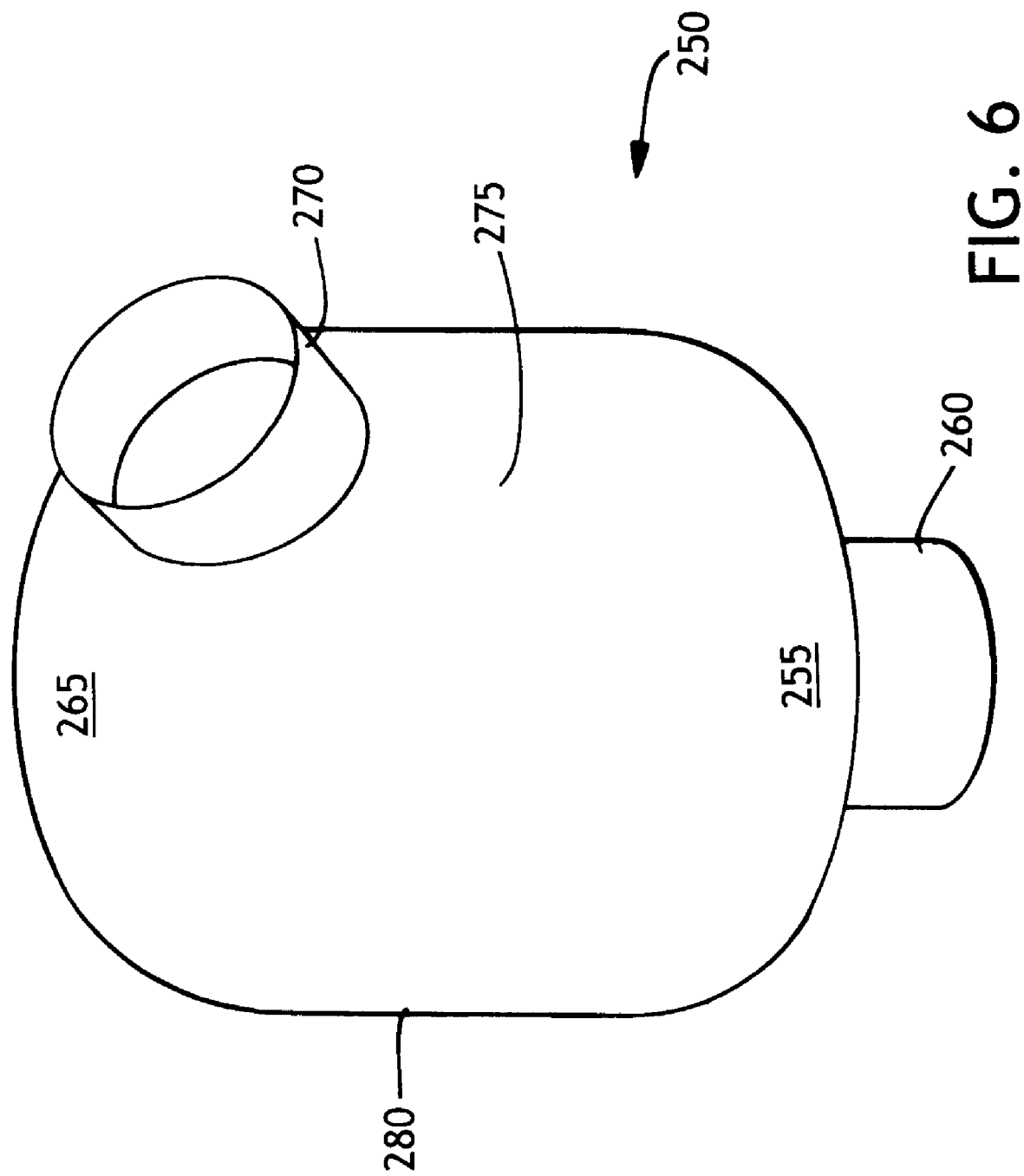
FIG. 6 is a perspective view of another embodiment of an exemplary inflatable balloon component.
Figure 7:
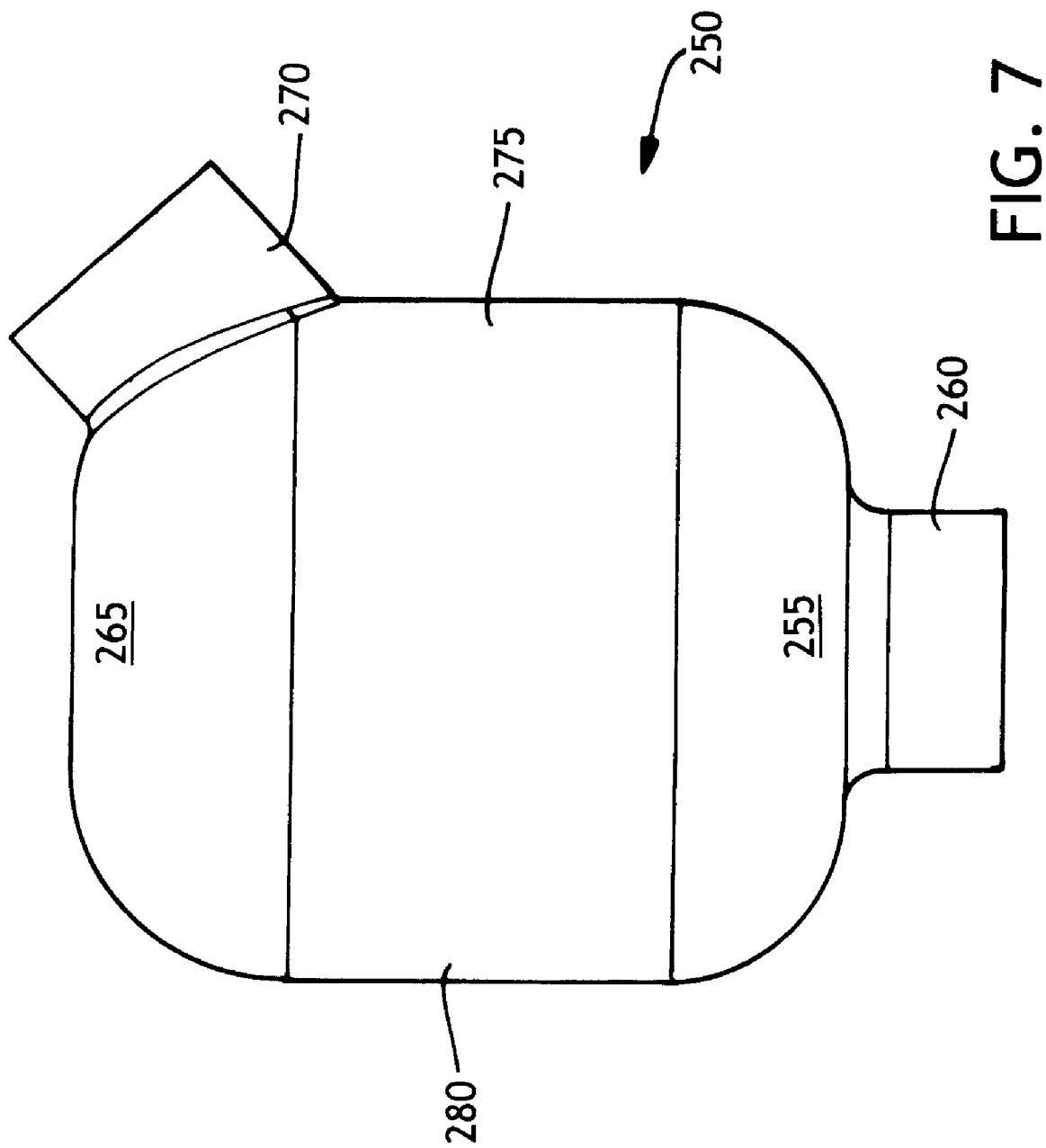
FIG. 7 which is a side view of another embodiment of an exemplary inflatable balloon component.

Referring again to FIG. 4 which as perspective view of the resulting inflatable balloon component 250 and FIG. 5 which is a side view of the same balloon, the inflatable balloon may include a distal end 255, a distal attachment zone 260, a proximal end 265, a proximal attachment zone 270, an upper region 275 and a lower region 280. As discussed above, the upper region desirably has a thickness of from about 15 to about 30 micrometers and the lower region desirably has a thickness of from about 5 to about 15 micrometers. FIG. 6 is a perspective view of another embodiment of an inflatable balloon component 250 and FIG. 7 is a side view of the same balloon. As can be seen in FIGS. 6 and 7, the inflatable balloon may include a distal end 255, a distal attachment zone 260, a proximal end 265, a proximal attachment zone 270, an upper region 275 and a lower region 280. The balloon of FIGS. 6 and 7 is formed in the same general manner as that of FIGS. 4 and 5; raw tubing is inserted in a mold so that the tubing travels through the mold in a straight line. The attachment of the formed balloon to the trach tube results in the proximal and distal balloon openings being offset from 180 degrees from each other.

The upper region shown in FIGS. 4 through 7 desirably has a thickness of from about 15 to about 30 micrometers and the lower region desirably has a thickness of from about 5 to about 15 micrometers. The dimensions of the balloon from the upper region 275 to the lower region 280 may range from about 50 millimeters to about 25 millimeters and may desirably be between about 35 millimeters to about 30 millimeters. The dimensions from the distal end 255 to the proximal end 265 may range from about 60 millimeters or more to about 25 millimeters and may desirably be between about 40 millimeters to about 30 millimeters. Of course, it is contemplated that the dimensions may be larger or smaller.

One advantage of having an inflatable balloon cuff having walls that are 30 microns or less (e.g., from 15 to 30 microns in the upper region to about 5 to 15 microns in the lower region) or even much less is that such a cuff presents a much lower profile and lies tighter to the shaft prior to inflation than balloons having thicker membranes, e.g. those thicker than 30 microns. Conventional thick balloons provide substantial additional material that needs to pass through the tracheal stoma during insertion. This additional material requires a larger stoma through which to pass, creating increased trauma and possibly affecting the eventual outcome of the patient.

The raw tube may also have an asymmetric wall thickness. An illustration of cross-section of an asymmetric raw tube 300 is shown in FIG. 8A and FIG. 8B. The degree of asymmetry of the central lumen 302 will depend on factors such as the type of thermoplastic polymer and the amount of blowing and or stretching the tube will be subjected to. Due to its asymmetry, the tube may be rotated prior to blowing so that the resulting balloon wall thickness profile may be fine tuned by the user for specialty applications. The wall thickness at different points in the balloon may be even more different than that of a balloon made in the same way with symmetrical tubing. Alternatively the tubing may be oriented in an asymmetrical mold so that the wall thicknesses at different points in the balloon are nearly the same.

This application is one of a group of commonly assigned patent application which are being filed on the same day. The group includes application Ser. No. 12/206,517 in the name of Brian Cuevas and is entitled "Improved Balloon Cuff Tracheostomy Tube"; application Ser. No. 12/206,560 in the name of Brian Cuevas and is entitled "Improved Balloon Cuff Tracheostomy Tube with Greater Ease of Insertion"; application Ser. No. 12/206,480 in the name of Brian Cuevas and is entitled "A Tubular Workpiece for Producing an Improved Balloon Cuff Tracheostomy Tube"; application Ser. No. 12/206,583 in the name of Brian Cuevas and is entitled "A Method of Making an Improved Balloon Cuff Tracheostomy Tube";

Modifications and variations of the present invention will be obvious to those of skill in the art from the foregoing detailed description. Such modifications and variations are intended to come within the scope of the following claims.

We claim:

1. A method for making a balloon having differential wall thickness comprising the steps of:
   placing a raw tube having a lumen in an asymmetrical mold, said mold having an opening on each end through which the tube protrudes;
   holding said tube tightly on each end of said mold;
   preheating said mold and tube to a temperature between 50 and 120 ° C.;
   stretching said tube about 50 to 200 percent over a time period of between 5 and 60 seconds with pressure applied internally with air, nitrogen or another inert gas at about 0.5 bar, while the temperature is maintained;
   pressurizing said tube with pressure applied internally with air, nitrogen or another inert gas at a pressure between about 0.5 and 2 bar while allowing said tube to retract lengthwise by 10 to 50 percent over a time period of between 5 and 15 seconds, to form a balloon;

heating the tube while still in the mold with its ends held tightly, to a temperature of 130-165 ° C. for a time of about 30-90 seconds and at a pressure to keep the balloon inflated;

cooling said balloon at about 20-50 ° C.;

collapsing said balloon so that it may be withdrawn without damage;

removing said balloon from said mold;

wherein the completed balloon has differential wall thicknesses, consisting of a continuous upper region having a thickness of from 15 to about 30 micrometers and consisting of a continuous lower region having a thickness of from about 5 to 15 micrometers.

2. The method of claim 1 wherein said raw tube comprises a thermoplastic polymer, said tube having an asymmetric wall thickness.

3. The method of claim 2 wherein said thermoplastic polymer is selected from the group consisting of thermoplastic polyurethane polymers, thermoplastic polyolefin elastomers, thermoplastic polyolefin block copolymers, SBS di-block elastomers, SEBS tri-block elastomers, polyvinyl chloride, low density polyethylene, polyethylene terephthalate and blends and mixtures thereof.

* * * * *